United States Patent [19]

Hill et al.

[11] Patent Number: 4,781,742
[45] Date of Patent: Nov. 1, 1988

[54] METHOD AND APPARATUS FOR DETECTING UNWANTED MATERIALS AMONG CULLET

[75] Inventors: Barry R. Hill, St. Helens; David M. Ring, Southport, both of England

[73] Assignee: Pilkington PLC, St. Helens, England

[21] Appl. No.: 96,523

[22] Filed: Sep. 15, 1987

[30] Foreign Application Priority Data

Sep. 26, 1986 [GB] United Kingdom ............... 8623213

[51] Int. Cl.$^4$ ............................................. C03B 3/00
[52] U.S. Cl. ......................................... 65/29; 65/160; 65/335; 198/437
[58] Field of Search ............... 65/28, 29, 160, 335; 198/395, 437

[56] References Cited

U.S. PATENT DOCUMENTS

| | | | |
|---|---|---|---|
| 3,938,976 | 2/1976 | Walker | 65/335 X |
| 4,145,202 | 3/1979 | Grodin et al. | 65/335 X |
| 4,582,520 | 4/1986 | Sturm | 65/29 X |
| 4,585,343 | 4/1986 | Schave et al. | 65/29 X |

FOREIGN PATENT DOCUMENTS

| | | |
|---|---|---|
| 0231027 | 5/1987 | European Pat. Off. |
| 703694 | 2/1954 | United Kingdom . |
| 1305192 | 1/1973 | United Kingdom . |
| 1315654 | 5/1973 | United Kingdom . |
| 1520858 | 8/1978 | United Kingdom . |

OTHER PUBLICATIONS

Automating the Transporting and Charging of Batch and Cullet into a Tank Furnace, Budov et al, Glass & Ceramic (U.S.A.), vol. 28, #1,2, Feb. 1971, pp. 212-214.

Primary Examiner—Robert L. Lindsay
Attorney, Agent, or Firm—Burns, Doane, Swecker & Mathis

[57] ABSTRACT

An apparatus and a method for inspecting cullet for the presence of unwanted materials among the pieces of glass. A light source such as a laser directs light onto the cullet. At least one array of at least two light detectors is positioned to detect reflected light from the cullet. The detectors differentiate between non-uniformly scattered light from the cullet and generally uniformly scattered light from the debris. Signalling means are provided to signal the differentiation thereby to indicate the presence of debris in the cullet under inspection. When cullet is present on a moving cullet belt, light from the light source is intermittently scanned over the cullet in a raster-type scan. A multi-faceted rotatable mirror may be employed intermittently to reflect light onto the cullet.

19 Claims, 4 Drawing Sheets

METHOD AND APPARATUS FOR DETECTING UNWANTED MATERIALS AMONG CULLET

BACKGROUND OF THE INVENTION

This invention relates to detecting unwanted materials, such as refractory pieces or other debris, among cullet which is to be fed to a glass melting tank.

Cullet comprises pieces of broken glass which, in flat glass production, generally originate from breaking up defective sheets or ribbon. These broken pieces of glass which comprise the cullet are usually collected into piles and then used to feed the glass melting tank to avoid wastage of the glass and assist the melting operation. Other sources of cullet stem from accidental breakages at e.g. building sites when buildings are being glazed; or in glass container production from the collection of broken bottles which are required to be recycled. Whatever the source of the cullet is it will be apparent that any unwanted materials must be removed from the cullet before it is fed back into a glass melting furnace. This is relatively simple if the unwanted materials comprise ferrous or non-ferrous metal since a suitable metal detector can be employed to indicate the presence of metal among the cullet. However, non-metallic unwanted materials among cullet are more difficult to distinguish from the glass cullet.

Heretofore, when required the inspection of cullet for the presence of non-metallic unwanted materials has been generally carried out with the unaided eye and when located such materials are physically removed from the cullet prior to re-cycling of the cullet into the glass melting tank. There exiss a need for apparatus which will detect the presence of unwanted materials such as pieces of refractory or other debris among cullet but there are obvious difficulties in achieving this end, which difficulties are not encountered when inspecting a glass sheet or ribbon. An example of apparatus which can inspect for faults in a glass sheet or ribbon is described in UK patent specification No. 1315654, the disclosure of which is incorporated herein by reference. The patent teaches the use of a laser system which scans laser light across the sheet or ribbon as it is moving. A light detector is positioned underneath the sheet or ribbon in a position remote from the normal light entry and exit paths of the light beam from the laser. When the light beam impinges upon a defect the light beam is scattered away from the normal light entry and exit path and part of this scattered light is detected by the light detector. The light detector thus gives a signal indicative of the presence of the defect.

Although it might be desirable if apparatus such as is described in UK Pat. No. 1315654 could be used for the detection of unwanted materials among cullet, there are obvious difficulties in differentiating between light scattered by the cullet itself and light scattered by unwanted materials such as refractory debris. It is perhaps for this reason that heretofore no automatic method or apparatus using a light beam has to the present inventors' knowledge been satisfactorily employed for the detection of refractory or other debris among cullet. It is an object of the present invention to provide such method and apparatus.

SUMMARY OF THE INVENTION

According to a first aspect of the invention there is provided apparatus for inspecting cullet for the presence of unwanted materials among the pieces of glass, the apparatus comprising a light source such as a laser for directing light onto the cullet, at least one array of at least two light detectors positioned to differentiate between light which is not scattered uniformly from the cullet, which light is indicative of reflections off the cullet itself, and light which is scattered generally uniformly, which uniformly scattered light is indicative of the presence of unwanted material such as refractory debris among the cullet, and signalling means to signal said differentiation to thereby indicate if unwanted material is or is not present among the cullet under inspection.

According to a second aspect of the invention there is provided an automatic method of inspecting cullet for the presence of unwanted materials among the pieces of glass, the method comprising the steps of directing light from a light source such as a laser onto the cullet, detecting reflections therefrom by means of at least one array of at least two light detectors, with the or each array differentiating between light which is not scattered uniformly from the cullet, which light is indicative of reflections of the cullet itself, and light scattered generally uniformly, which uniformly scattered light is indicative of the presence of unwanted material such as refractory debris among the cullet, and signalling said differentiation to thereby indicate if unwanted material is or is not present among the cullet under inspection.

The invention thus provides means for discriminating between reflections of light from glass cullet, which reflections are generally in discrete directions, and scattered light from unwanted material such as refractory debris, which light is scattered in all directions in a generally uniform manner. This is possible as a result of the appreciation that there is usually a fundamental difference in the distribution of light reflected by pieces of broken glass comprising cullet and light scattered by e.g. pieces of refractory material. In the case of the latter, all of the light detectors in the or each array will receive part of the scattered beam and thus produce an electrical signal indicative thereof. Thus, in circumstances where all of the light detectors in the or each array provide simultaneous electrical signals, this indicates that the light has been scattered from e.g. pieces of refractory debris. In contradistinction, in the case of the former situation where the light is reflected off a piece of broken glass then it will be apparent that not all of the light detectors in the or each array are likely to receive such reflections and hence provide simultaneous electrical signals. Thus, the present invention neatly and simply solves the difficult problem of distinguishing between cullet and debris among cullet which has heretofore existed.

Preferably, the light source is scanned over the cullet in a raster-type scan and this may be achieved in either of two ways. The first method employed may be applicable to the situation where the cullet is moving during inspection, for example on a cullet conveyor belt which is usually the case. In these circumstances, it is only necessary to provide a single line scan across the cullet at repeated intervals. Conveniently, such a scan may be achieved by the use of a multi-faceted rotatable mirror attached to an electrically driven motor and arranged so that for each revolution of the motor the light from the light source is scanned across the cullet belt a number of times corresponding to the number of mirror facets.

The second way of achieving a raster-type scan is more applicable to the situation where the cullet is stationary relative to the light source. In these circumstances, the raster-type scan can be simply achieved by means of a pair of mutually orthogonal galvanometrically-driven mirrors of conventional type which may provide a raster scan of, typically, one hundred lines.

It will be appreciated that the number of light detectors in the or each array determines the reliability in terms of false-alarm rate, of the method or apparatus of the invention and, accordingly, preferably there are at least four light detectors associated with the or each array. Adjacent arrays may share common light detectors, and each array may be switchable on or off so that, at any given instant, one array of light detectors is activated but adjacent arrays are not.

Conveniently, the apparatus and method may utilize a bank of arrays which extend across and above e.g. a cullet belt, each array being separately switchable during scanning to coincide at any given moment with the position of the scanned beam.

Preferably, means may be provided to distinguish between ambient light and light from the light source such that false signals are eliminated or at least minimised. Such means may comprise means to modulate light from the light source, which modulation may conveniently be achieved by cyclically varying the amplitude of the light from the light source and arranging for the apparatus to differentiate between ambient light and such modulated light.

It will be understood that the term "light" as used herein is not intended to be limited to the visible regions of the electro-magnetic spectrum but can include other parts such as the infra-red. Thus, when modulation of light from the light source is required it is particularly convenient to be able to switch the light source between high and low outputs, for example on and off, at, say, anything up to 100 KHz. This is clearly not always feasible with common light sources such as gas lasers which operate in the visible parts of the spectrum but is quite easily achieved if e.g. a solid-state laser is used, which operates in the near infra-red. Accordingly, a preferred method of light modulation makes use of high-speed switching between high and low outputs, e.g. on and off, of a solid-state laser which thus provides for amplitude modulation of light from the light source. By the use of appropriate electronic circuitry, as described hereafter, differentiation of amplitude modulated light and ambient light is easily achieved.

As an alternative to modulation of light from the light source as a means to distinguish between such light and ambient light, an optical filter such as a narrow-band filter could be used to effectively eliminate all light from each detector except light of the same wavelength as that of the light source.

Conveniently, a reference light detector is used to indicate the start of the or each scan of the light source over the cullet.

DETAILED DESCRIPTION OF THE PREFERRED EMBODIMENTS

Figure 1:
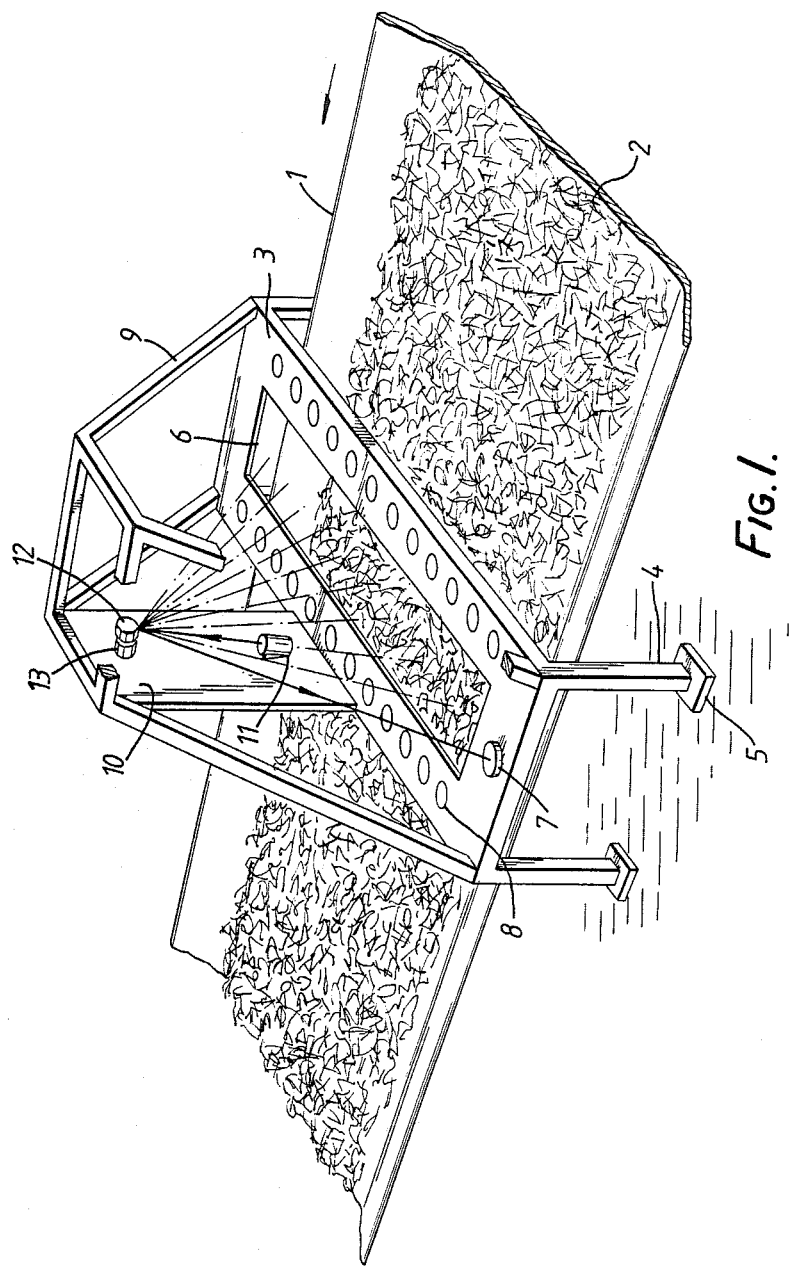
FIG. 1 is a schematic representation of apparatus according to the invention.

Referring firstly to FIG. 1 of the drawings, there is shown a cullet conveyor belt 1, transporting a stream of cullet 2 in the direction arrowed. Spanning the conveyor belt 1 is a bench which comprises a bench top 3 which is supported aobve the cullet belt 1 on legs and feet 4,5 at the four corners thereof. The bench top 3 has centrally therein a slotted opening 6. A single reference light-detector 7 is affixed to the top side of the bench top 3 adjacent one end thereof and aligned centrally with the slot 6.

On the bench top 3 on either side of the slot 6 are disposed respective columns of twelve sample light detectors 8 which project through to the underside of the bench top 3 and face the cullet 2 on the cullet belt 1.

Fixed above the bench top 3 is a frusto-triangular hood support 9 which, in use, normally carries a hood (not shown) comprised of metal sheet, which hood is used to protect the apparatus from the ingress of dirt etc. For clarity of illustration, part of the frusto-triangular hood support 9 is shown removed.

Extending upwardly from a central portion of the bench top 3 is a back plate 10 which is fixed at its other end to the top part of the hood support 9. The back plate 10 carries a solid state laser 11 arranged to direct light upwardly therefrom towards a multi-faceted mirror scanner wheel 12 secured for rotation on the shaft (not shown) of a scanner motor 13 itself secured to the back plate 10 above the laser 11. An encoder (not shown) is fixed to the shaft of the motor 13 and is used to indicate the angular orientation of the scanner wheel 12 at any given instant.

In operation, a thin beam of light from the laser 11 is directed towards the underside of the mirror scanner wheel 12 which is rotated by the scanner motor 13. The mirror scanner 12 has eight reflective sides and thus for every revolution thereof, a thin beam of light from the laser 11 is successively scanned in an arcuate manner a total of eight times in the manner indicated in the drawing. Each such scan effectively sweeps a beam of light centrally through and along the slot 6 in the bench top 3 and thus, in this region, the light is able to successively traverse across the cullet 2 on the cullet belt 1. During each scan switching means (not shown) successively switches on and off arrays of detectors 8, each such array comprising a total of four detectors which are switched on and off in synchronism with the swepp of light during each scan so that at any particular point during each scan, an array of light detectors 8 immediately above the light beam is activated, whilst arrays to either side are de-activated. This is illustrated with reference to FIG. 2 of the accompanying drawings which shows a detailed schematic view of part of the apparatus of FIG. 1. In the drawing, for clarity of illustration only, the area covered by the first such array of light detectors 8 is designated "A", whereas the area covered by the second array is designated "B" and so on. Thus, when the beam of light from the scanner 12 is sweeping across that area of the cullet belt 1 designated "A" the four light detectors 8 immediately above the area are activated, whereas adjacent light detectors are de-activated. Similarly, when the beam of light from the scanner 12 is sweeping across the area designated "B" of the cullet belt 1 those light detectors 8 immediately above it are activated and light detectors 8 on either side are de-activated.

Figure 2:
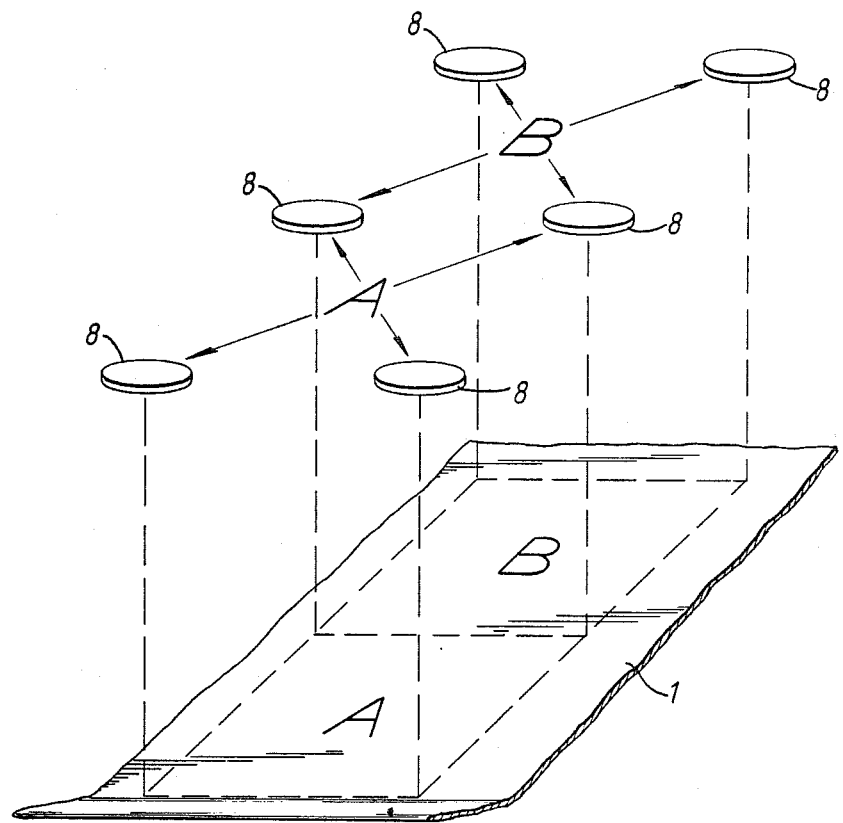
FIG. 2 is a detailed schematic view of part of the apparatus of FIG. 1.

It will be apparent from FIG. 2 that arrays "A" and "B" share a respective pair of light detectors 8 although it would, of course, be possible to substitute such an arrangement for an arrangement in which light detectors are specific to each array.

The reference light detector 7, shown in FIG. 1, is used to indicate the start of each successive scan so that, for each complete rotation of the scanner motor 13, eight such successive scans are identified.

If a piece of refractory material or other such unwanted debris is present among the cullet 2, scattered light from the surface of such material will normally impinge upon all four detectors in that array immediately above the unwanted material when the light sweeps across it. Signalling means (not shown) are connected to the apparatus which means are operable to indicate when such a condition exists and thereby provide a signal indicative of the presence of the unwanted material. The unwanted material can then be removed by an automatic diverting process occurring further down the cullet belt line.

By providing a number of detector arrays which are sequentially activated and de-activated to follow the progress of each scan of light the distance between respective detectors of each such array and the effective source of scattered light, i.e. the refractory piece or other debris is kept constant. This ensures that the signal output from the detectors in each array will be constant when receiving any such scattered light and will not vary greatly over the width of the scan.

Although in the embodiment described a laser is used to produce the beam of light it will be appreciated that other light sources can be used such as an incoherent but sufficiently intense beam of light.

Figure 3:
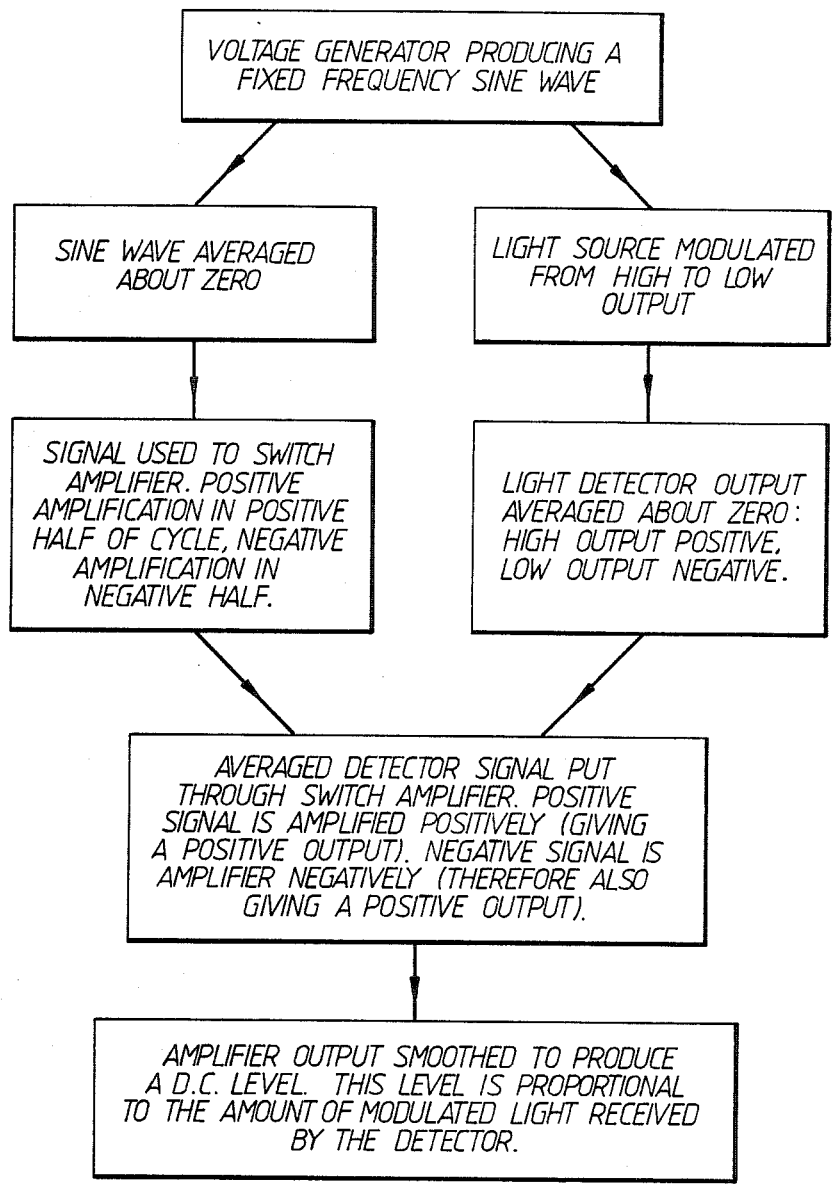
FIG. 3 is a flow diagram of a preferred method of operating the apparatus of FIG. 1.
Figure 4:
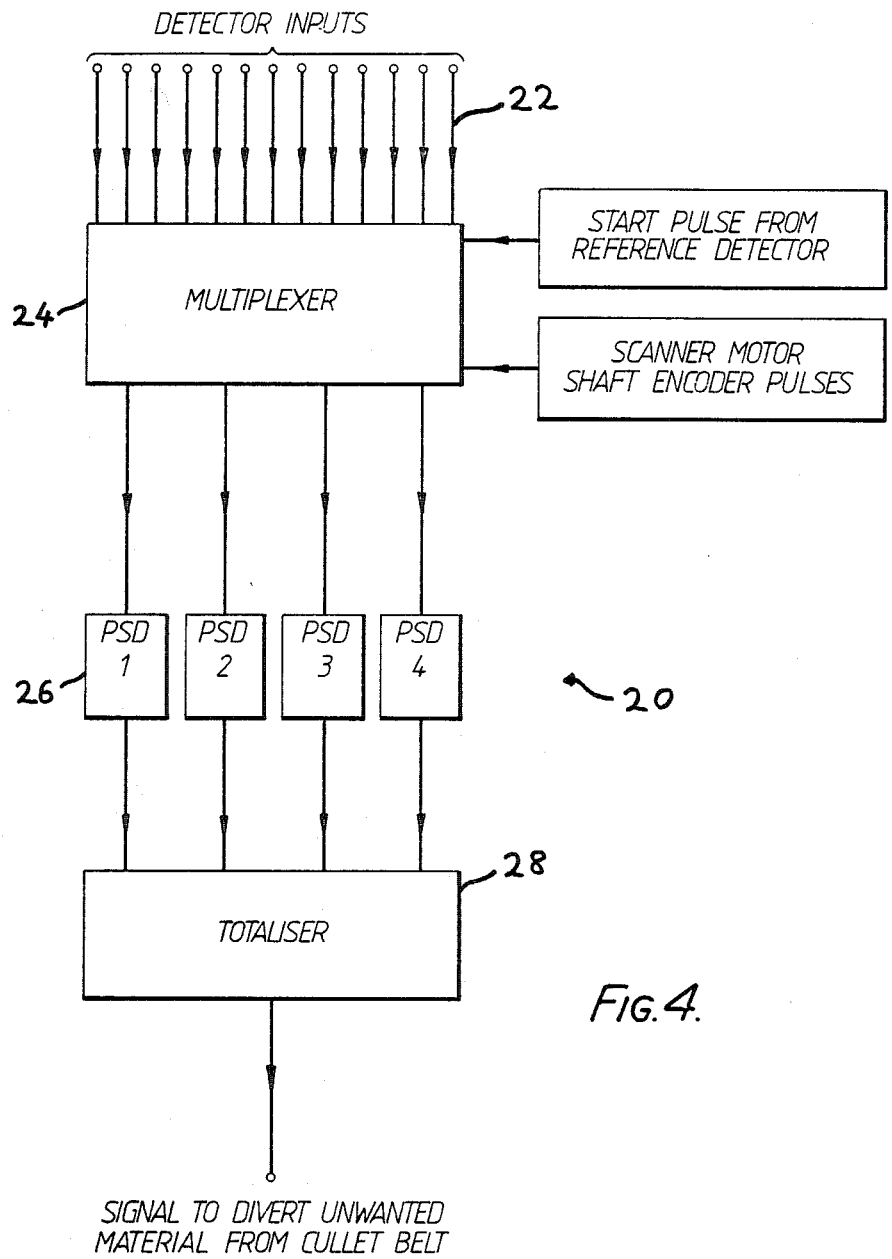
FIG. 4 is a simplified circuit diagram for use with the apparatus of FIG. 1

In FIGS. 3 and 4 of the drawings there is shown in more detail the method of operating the apparatus of FIG. 1, which method may be conveniently designated as phase sensitive detection and for such a system to work light from the light source 11 must vary in intensity with time.

FIG. 3 is a flow diagram of a preferred method of operating the apparatus of FIG. 1, in which a voltage generator produces a fixed frequency sinusoidal waveform which is then used to modulate the light source from a high to a low output of light. This modulated light produces a corresponding modulation in each light detector, which corresponding modulation is itself averaged about zero so that the high output produces a positive signal and the low output produces a negative signal. The original fixed frequency sinusoidal waveform is then used as a reference. It is also averaged about zero and this averaged signal is used to switch in an amplifier providing for positive amplification in the positive half of the sinusoidal waveform cycle and negative amplification in the negative half of the cycle. The averaged signals from the detectors are then put through the switched amplifier such that the positive signal is amplified positively giving a positive output, and the negative signal is amplified negatively, therefore also giving a positive output. Following on from this, the amplifier output is smoothed to produce a DC level of voltage which is proportional to the amount of modulated light received by each light detector.

In FIG. 4 is a schematic diagram of a circuit 20, comprising the signalling means referred to hereinabove, for use with the apparatus which shows the twelve detector inputs 22 into a multiplexer 24 which also receives an input from the reference detector 7 which is used as a start pulse input. The encoder on the shaft of the scanner motor 13 provides a series of electrical pulses and in this case the pulses are generated every time the shaft of the motor 12 turns through approximately three quarters of one degree, thus giving for each complete revolution a total of 500 pulses. These pulses are used to monitor the rotational position of the scanner 13 so that in turn the position of the beam on the cullet belt 1 will be known at any given instant.

The multiplexer 24 provides full output to four phase-sensitive detection circuits 26 marked PSD 1 to 4 respectively and each of these circuits is in turn connected to a totaliser circuit 28 which gives an electrical output if all four inputs from the phase sensitive detection circuits 26 PSD 1 to 4 are above the required threshold level. The totaliser circuit 28 then provides a signal to a cullet belt diverter (not shown) of conventional form which diverts from the cullet belt 1 that part of the cullet 2 identified previously as having unwanted material present among it. It will be apparent from the foregoing that other types of circuitry can be used to operate the apparatus in accordance with the invention which may or may not, as the case may be, include phase sensitive detection circuits 26 if modulation of the light source is required.

The present invention has particular application for detecting pieces of refractory material in cullet which is to be employed for the manufacture of rolled plate glass. The present invention may also be employed in conjunction with a float glass plant where it is used to detect debris such as polystyrene spacers (which are used to stack glass sheets), protective gloves, wooden poles, plastic cups, cardboard, paper, etc. which can inadvertently be dropped into the cullet. Furthermore, the present invention can also be used to detect pieces of concrete which can sometimes be present in cullet, particularly cullet which comes from building sites.

We claim:

1. An apparatus for inspecting glass cullet for the presence of unwanted materials among the pieces of glass, the apparatus comprising frame means disposed adjacent the cullet, a light source mounted on the frame means for directing light onto the cullet to simultaneously illuminate glass particles and unwanted particles which may be present, at least one array of a plurality of light detectors mounted on the frame means and positioned to differentiate between light which is scattered from the cullet with sufficient lack of uniformity to be indicative of reflections off the cullet itself, and light which is scattered with sufficient uniformity to be indicative of reflections off unwanted material among the cullet, and signaling means operably connected to said detectors to provide an indication of the presence of unwanted material among the cullet.

2. An apparatus according to claim 1, further comprising scanning means for scanning light from said source over the cullet in a raster-type scan.

3. An apparatus according to claim 2, wherein the scanning means comprises a multi-faceted rotatable mirror and an electrically driven motor which is arranged to rotate the mirror, the arrangement being such that, in use, light from the light source is directed onto the mirror and reflected therefrom onto the cullet whereby for each revolution of the motor the light from the light source is scanned across the cullet a number of times corresponding to the number of mirror facets.

4. An apparatus according to claim 2, wherein said at least one array comprises a bank of arrays which extends across and above a cullet support, each array being separately switchable during scanning to coincide at any given moment with the position of the scanned light beam.

5. An apparatus according to claim 4, wherein each array includes at least four light detectors in the respective array.

6. An apparatus according to claim 5, having adjacent arrays which share common light detectors.

7. An apparatus according to claim 6, comprising means for switching each array on or off whereby a given individual array can be selectively activated while adjacent arrays are unactivated.

8. An apparatus according to claim 2, further comprising a reference light detector for indicating the start of each scan of light from said source over the cullet.

9. An automatic method of inspecting glass cullet for the presence of unwanted materials among the pieces of glass, the method comprising the steps of directing light onto the cullet from a light source mounted on frame means adjacent the cullet to simultaneously illuminate glass particles and unwanted particles which may be present, detecting reflections therefrom by means of at least one array of a plurality of light detectors mounted on the frame means, with the array differentiating between the light which is scattered from the cullet with sufficient lack of uniformity to be indicative of reflections off the cullet itself, and light scattered with sufficient uniformity to be indicative of reflections off unwanted material among the cullet, and providing an indication of the presence of unwanted material among the cullet by signaling means operably connected to the light detectors.

10. A method according to claim 9, wherein the directing step comprises scanning light from the light source over the cullet in a raster-type scan.

11. A method according to claim 10, comprising moving the cullet relative to the light source during inspection the scanning step performed such that light from the light source scans in a single line scan across the cullet at repeated intervals.

12. A method according to claim 9, further comprising distinguishing between ambient light and light from the light source.

13. A method according to claim 12, wherein the distinguishing is effected by modulating light from the light source and differentiating between ambient light incident on the detectors and such modulated light incident on the detectors.

14. A method according to claim 13, wherein the modulation is effected by cyclically varying the amplitude of the light from the light source.

15. A method according to claim 13, wherein the light source comprises a solid state laser and the modulation is effected by switching the laser between high and low outputs.

16. A method according to claim 12 wherein light from the light source and ambient light are distinguished by filtering light which is incident on the detectors thereby substantially to eliminate all light from each detector except light of the same wavelength as that of the light source.

17. A method according to claim 11, further comprising indicating the start of each scan of light from the light source over the cullet.

18. Apparatus according to claim 1 in which said light source is a laser.

19. Apparatus according to claim 4 in which said cullet support is a belt.

* * * * *